United States Patent [19]

Blackmer

[11] 4,278,082
[45] Jul. 14, 1981

[54] ADJUSTABLE NASAL CANNULA

[76] Inventor: Richard H. Blackmer, 109 Oakwood Dr., Scotia, N.Y. 12302

[21] Appl. No.: 38,287

[22] Filed: May 11, 1979

[51] Int. Cl.³ .............................................. A61M 15/08
[52] U.S. Cl. ........................... 128/207.18; 128/DIG. 9
[58] Field of Search ........................ 128/207.18, 203.22

[56] References Cited

U.S. PATENT DOCUMENTS

| 2,693,800 | 11/1954 | Caldwell | 128/207.18 |
| 3,400,714 | 9/1968 | Sheridan | 128/207.18 |

FOREIGN PATENT DOCUMENTS

| 1124404 | 10/1956 | France | 128/207.18 |

Primary Examiner—Henry J. Recla
Attorney, Agent, or Firm—Dennis H. Lambert

[57] ABSTRACT

A nasal cannula is disclosed which may be easily and quickly adjusted to custom fit individual wearers. The nasal cannula comprises lengths of tubing with the ends formed to provide narine tubes which project into the nares of the wearer, and does not have any cavity-forming structure which might promote growth of bacteria or result in resonant flow noises. The formed ends of the tubing are secured to a formable bridge or saddle which spans the distance between the narine tubes, whereby the angular position as well as the spacing between the narine tubes may be quickly and easily adjusted by suitably forming the bridge.

9 Claims, 12 Drawing Figures

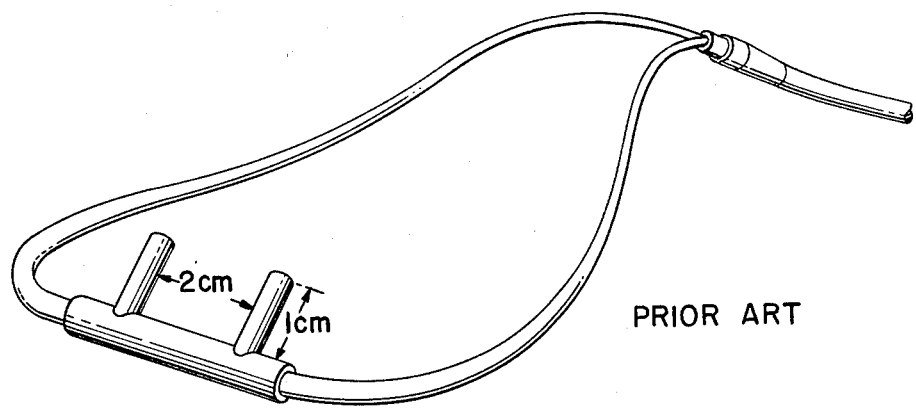
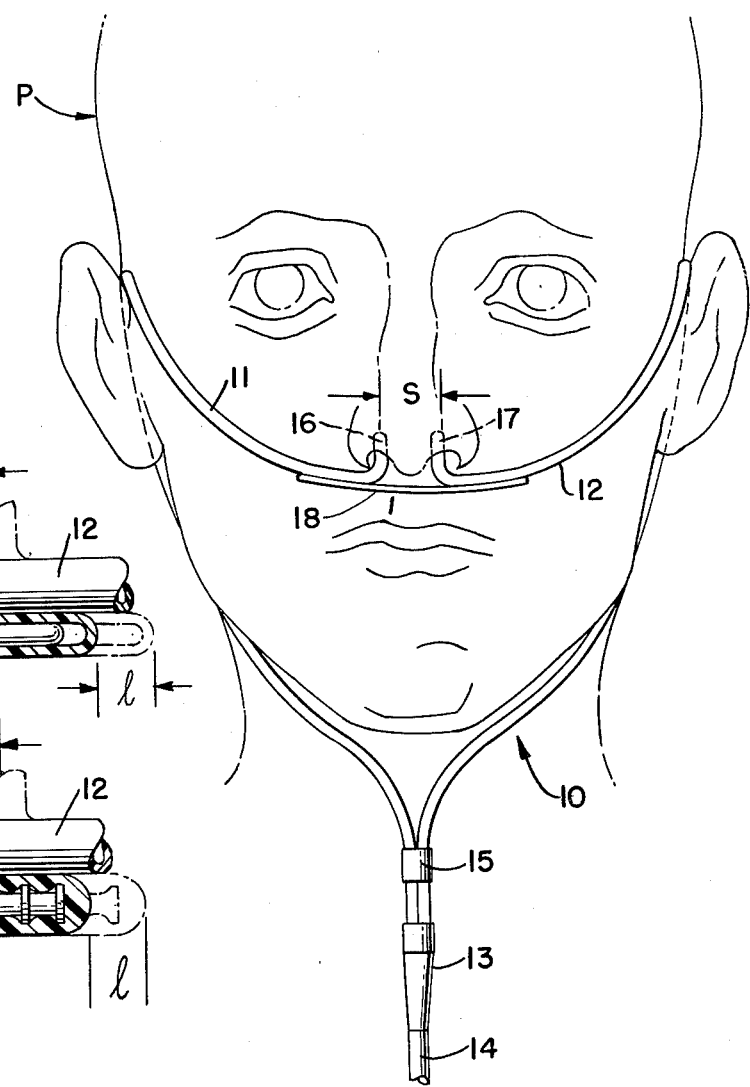
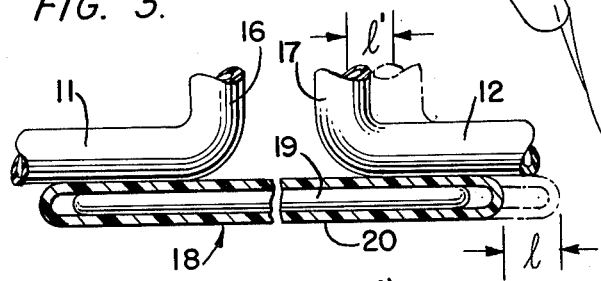
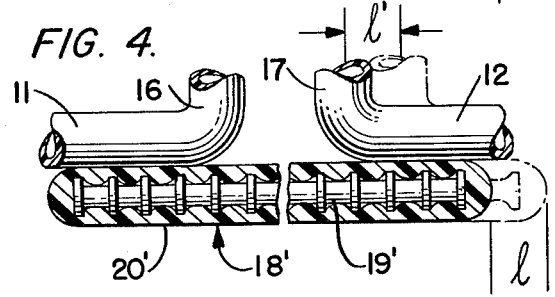

ADJUSTABLE NASAL CANNULA

BACKGROUND OF THE INVENTION

This invention relates to apparatus for administering oxygen or other gas to a patient, and more particularly, relates to such apparatus in the form of nasal cannulae having narine tubes which project into the nares of the patient.

Prior art nasal cannulae typically comprise two tubular narine prongs projecting perpendicularly from opposite ends of a tubular cannula body and extending generally parallel to one another for insertion into the nares of the patient, with the cannula body secured against the nose and upper lip by support tubing which loops over each ear of the patient, or by a headband extending around the head of the patient. Other types of prior art nasal cannulae are disclosed in U.S. Pat. Nos. 2,931,358 and 3,726,275. In U.S. Pat. No. 2,931,358 lengths of tubing 30 are extended at one of their ends through holes provided in a bridge member 6 whereby the terminal ends of the tubing are held in a predetermined spaced apart, parallel relationship for entry into the nares of the patient. Adjustment of the spacing between the narine tubes is accomplished by insertion of the narine tubes through different openings in the bridge member. U.S. Pat. No. 3,726,275 discloses an arrangement wherein two lengths of tubing are crossed over at the narine ends thereof, and secured in fixed relationship relative to one another by cement or adhesive or the like, and a ring 24 placed around the crossed-over portions of the tubing. The narine tubes 12 and 16 in this patent are adapted to flex or move within limits upon facial movement of the patient using the nasal cannulae. Still other prior art devices are exemplified in U.S. Pat. Nos. 2,693,800 and 3,513,844.

Most prior art nasal cannulae are manufactured from highly plasticized PVC or similar plastics, and in most cases have relatively heavy and bulky bridge members which are both unsightly and uncomfortable to the user.

SUMMARY OF THE INVENTION

An object of the invention is to provide an improved nasal cannula which is quickly and easily form-fitted to individual users.

Another object of the invention is to provide a nasal cannula which is free of cavity-forming structures which might promote growth of bacteria or result in resonant flow noises.

A still further object of the invention is to provide a nasal cannula for administering oxygen or other gas to a patient wherein the cannula is formed of non-allergenic, sterilizable materials.

An even further object of the invention is to provide a nasal cannula which has good cosmetic appearance and yet is capable of delivering desired amounts of gas to the wearer.

Yet another object of the invention is to provide apparatus for delivering oxygen or other gas to a patient wherein the apparatus includes nasal cannulae which may be formed as desired to deliver oxygen or other gas simultaneously to the nostrils of the patient and to the mouth of the patient.

A further object of the invention is to provide cannulae for delivering oxygen or other gas to a patient wherein the cannula are light in weight and may be formed to deliver oxygen or other gas to the mouth of the patient by utilization of the Coanda effect.

A still further object of the invention is to construct nasal cannulae from continuous tubing thereby permitting fabrication from silicone and other materials.

Accomplishment of the above objects is made with the present invention by provision of continuous lengths of tubing such as PVC tubing or silicone tubing and the like, having ends thereof permanently formed or shaped to define narine tubes, wherein a formable bridge member is secured to the narine tube ends of the flexible tubing, whereby upon suitable formation of the formable bridge member the angular relationship between the narine tubes may be readily adjusted as well as the spacing therebetween to precisely fit the nasal cannulae to different patients.

The formable bridge member may comprise either a bendable wire member covered with a plastic material and suitably secured to the tubing at the narial ends thereof or it may comprise a corrosion-resistant wire having its opposite ends inserted into the narine tubes. Moreover, the plastic material covering the wire member in the bridge may be slipped relative to the wire member whereby the lateral spacing between the narine tubes may be adjusted.

BRIEF DESCRIPTION OF THE DRAWINGS

FIG. 1 is a perspective view of a prior art device.

FIG. 2 is a front view in elevation of a first form of nasal cannula according to the invention.

FIG. 3 is a greatly enlarged, fragmentary view with portions in section of a first form of bridge structure used in the cannula of the invention.

FIG. 4 is a view similar to FIG. 3, of a second form of bridge structure.

DETAILED DESCRIPTION OF THE PREFERRED EMBODIMENTS

Figure 5:
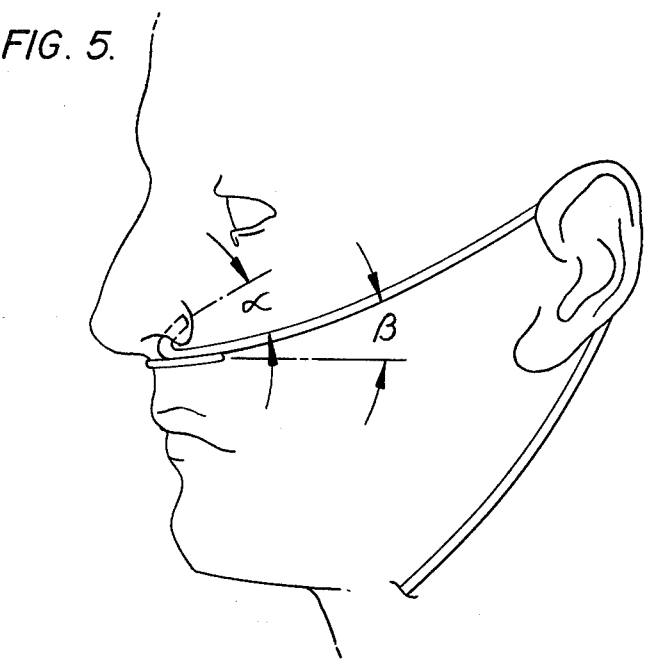
FIG. 5 is a side view in elevation of the nasal cannula of FIG. 2.

In the drawings, wherein like reference numerals indicate like parts throughout the several views, a first form of nasal cannula in accordance with the invention is indicated generally at 10, and comprises a pair of lengths of substantially continuous, constant diameter flexible tubes 11 and 12 bonded at one of their ends in a tubing connector 13 which is joined with a length of tubing 14 for delivering gas from a source to the tubes 11 and 12. A slip ring 15 is fitted over the tubes 11 and 12 near the connector 13 for tightening or adjusting the loop formed by the tubes 11 and 12 relative to the body of the user or patient indicated generally at P.

The other ends of the tubes 11 and 12 are permanently formed or bent to define normally curved, relatively short narine tubes or projections 16 and 17 extending generally parallel to one another and permanently secured to a formable bridge member 18. As fabricated and packaged, the bridge member 18 is straight and the narine projections or tubes 16 and 17 are spaced apart a nominal distance corresponding to the average spacing or spread S of the nares.

Figure 6:
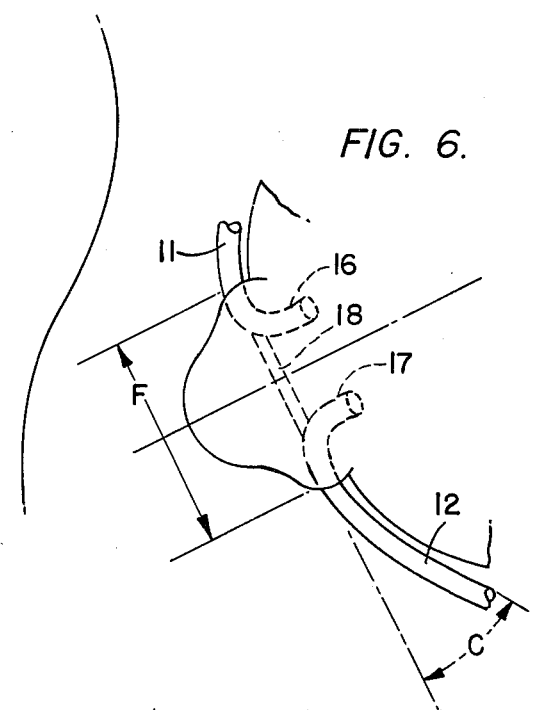
FIG. 6 is a fragmentary, plan view of the cannula of FIG. 5.

In use, a nurse or therapist fits the cannula to each patient by estimating the naris-ear angle $\alpha$ (FIG. 5) and bending the cheek angle C (FIG. 6) at the nostril flare dimension F (FIG. 6). The cheek angle C is bent in the nostril-ear reference plane established by the vertical nostril-ear angle $\beta$ (FIG. 5) between the nostrils and the top crotch of the ear. The cannula is then secured to the patient by looping the tubes 11 and 12 over the ears of the patient and sliding the slide-ring 15 upwardly relative to the neck or chin of the patient.

Alternatively, the slide-ring 15 and associated tubing could be positioned at the back of the patient, if desired.

The narine tubes 16 and 17 are located and vertically directed in the nares with relative precision because of the rigidity of the cannula bridge 18, and the stable nose-ear geometry.

Horizontal spacing or positioning of the narine tubes 16 and 17 is determined by fit to the nasal flare F or tube contact with the septum.

As seen in FIGS. 3 and 4, the bridge 18 (or 18', FIG. 4) comprises a pliable, shape retaining wire 19 (19', in FIG. 4) covered with a plastic sheath 20 (20', in FIG. 4). The plastic sheath has a strong friction fit with the wire in each of the forms of the invention in FIGS. 3 and 4, whereby the parallelism and spacing between the narine tubes 16 and 17 may be adjusted by twisting the tubes and plastic sheath 20, 20' relative to the wire core 19, 19'. In other words, the tubes and associated tubing may be grasped and moved apart, stretching the plastic sheath, which will then remain in its stretched position due to the friction fit between the sheath and the wire core. Additionally, in the form of the invention shown in FIG. 4, the wire core 19' is serrated or formed with a series of axially spaced rings or ribs, whereby when the plastic sheath 20' is stretched relative thereto it, in effect, is positively mechanically locked in the stretched position. A stretched position of the plastic sheath and of the narine tubes is indicated in dot-and-dash lines in FIGS. 3 and 4. Also, the bridge 18 or 18' may be bent to provide a desired relationship between the narine tubes 16 and 17.

Figure 7:
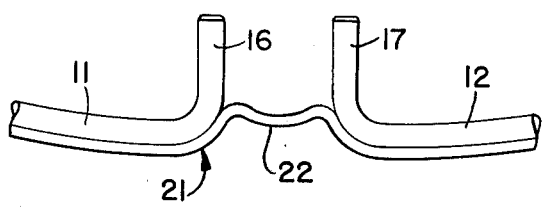
FIG. 7 is a fragmentary, plan view of a third form of the invention wherein the bridge structure comprises a formable saddle member.

A modified form of the invention is illustrated in FIG. 7, wherein the bridge comprises a saddle member 21 having a mid-portion 22 configured to cooperate with the septum in the patient's nose to provide more positive horizontal positioning of the narine tubes 16 and 17.

Figure 8:
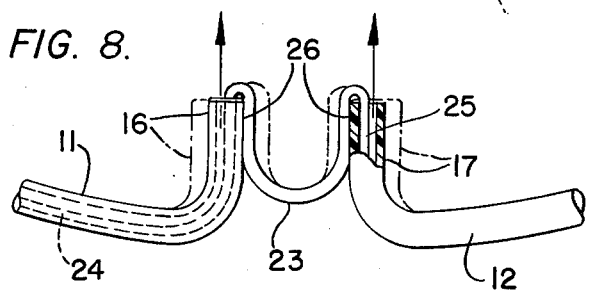
FIG. 8 is a view similar to FIG. 7 of a fourth form of the invention wherein a formable wire comprises the bridge member between the narine tubes.

A further modification is illustrated in FIG. 8, wherein a corrosion-resistant wire 23 has its opposite ends 24 and 25 inserted into the narine tubes 16 and 17. The central or bight portion of the wire 23 which spans the distance between the narine tubes 16 and 17 has its opposite legs extending parallel to the end portions 24 and 25 in the narine tubes 16 and 17 and the wire may be bonded to the outside of the narine tubes 16 and 17 in this area. Alternatively, the ends 24 and 25 may be barbed or otherwise provided with detent means for retaining the wire in position relative to the tubes.

Figure 9:
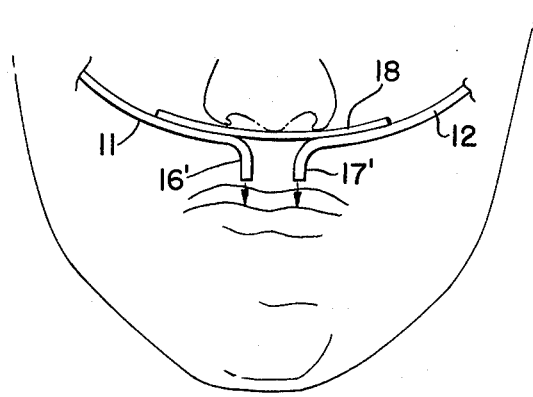
FIG. 9 is a fragmentary view showing the narine tubes bent downwardly to direct gas into the mouth of the user.

In FIG. 9, the invention is shown with the narine tubes 16' and 17' twisted or bent downwardly to direct gas into the mouth of the user. The flow of gas will cling to the upper lip due to the Coanda effect and will flow into the mouth when the inspiration rate exceeds the cannula flow rate.

Figure 10:
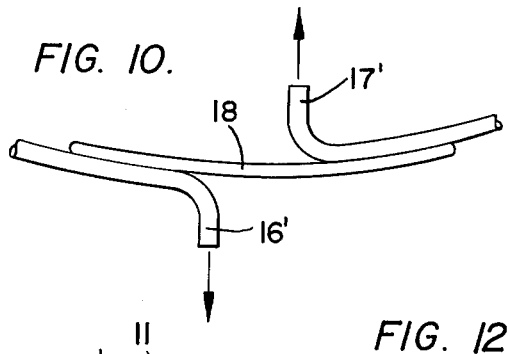
FIG. 10 is a fragmentary view of the narine tubes and bridge member showing one of the tubes bent upwardly to direct gas into the nostril of the user and the other tube bent downwardly to direct gas into the mouth of the user.

If desired, one narine tube may be bent downwardly at 16' and the other upwardly at 17' to simultaneously direct gas into the nostril and mouth of the user as illustrated in FIG. 10.

Figure 11:
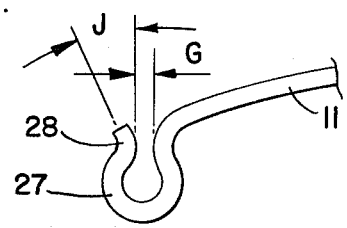
FIG. 11 is a fragmentary view of yet another form of the invention wherein the narine tube is formed as a clip to clip onto the flare of the nostril.
Figure 12:
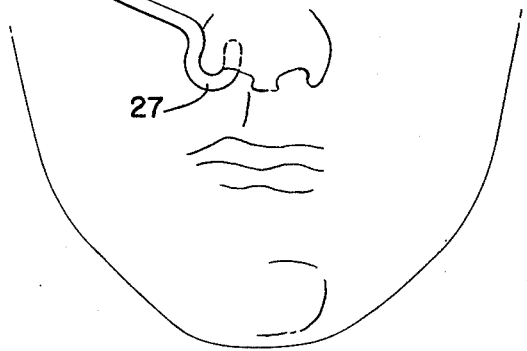
FIG. 12 is a view showing the form of the invention in FIG. 11 in use on a patient.

In FIGS. 11 and 12, a form of the invention is illustrated which is particularly suitable for daytime use if cosmetic considerations are important. In this form of the invention the tubing 11 is permanently formed at its end with a hook-shaped configuration 27 which is adapted to grip the flare of the nostril as illustrated in FIG. 12. Thus, the space G defined by the hook 27 is calculated to be less than the thinnest flare side of the nostril likely to be encountered. The narine end 28 of the hook may be cut off if desired to achieve a desired jet angle J to avoid impingement of gas against the side of the nares. It should be noted that in this form of the invention, the primary locating action is achieved by the delivery tubing 11 supported over the ear.

In one experiment performed with a nasal cannula according to the invention, two liters per minute of 100% oxygen was supplied to a subject while the subject was in a 10% oxygen environment, i.e., a nitrogen flooded helmet, and the blood oxygen saturation was monitored with a Hewlett-Packard Ear Oximeter. The subject's normal air saturation was 96% and dropped to below 80% in the nitrogen-rich atmosphere prior to initiating flow of supplemental oxygen via the cannula of the invention. After flow of oxygen was initiated with the invention, the blood oxygen saturation of the subject was maintained at 95%.

A similar test was performed by administering six liters per minute of 40% oxygen and the same blood oxygen saturation of 95% was maintained.

With the present inention, the position of the narine tubes in a patient's nares can be accomplished with precision and repeatability by simple bending operations on the cannula bridge in any desired direction, i.e. in any of three dimensions, or solid angular relationship, and once bent the cannula will retain the precision, custom fit to the particular patient.

As this invention may be embodied in several forms without departing from the spirit or essential characteristics thereof, the present embodiment is, therefore, illustrative and not restrictive, since the scope of the invention is defined by the appended claims rather than by the description preceeding them, and all changes that fall within the metes and bounds of the claims or that form their functional as well as conjointly cooperative equivalents are, therefore, intended to be embraced by those claims.

I claim:

1. A nasal cannula for delivering gas to a patient, comprising:
  a pair of lengths of substantially continuous, constant diameter flexible tubes having opposite ends and means on one of their ends for connection to a supply of gas;

the other ends of the tubes terminating adjacent to one another and being normally curved at an angle relative to the lengths of tubes to define a pair of form-retaining narine tubes for insertion into the nares of a patient; and a formable bridge means comprising a length of shape-retaining wire-like material secured to said tubes at said other ends in spanning relationship thereto for holding the narine tubes in predetermined solid angular and spaced relationship relative to one another, said formable bridge means being easily formed to change the angular and spaced relationship between the narine tubes.

2. A nasal cannula as in claim 1, wherein:
the bridge member comprises a bendable wire extended between the other ends of the tubes.

3. A nasal cannular as in claim 2, wherein:
a plastic sheath covers the wire and is frictionally engaged on the wire for limited movement relative thereto, whereby the narine tubes may be angularly adjusted relative to one another by twisting them relative to the wire.

4. A nasal cannular as in claim 3, wherein:
the plastic sheath is stretchable relative to the wire, whereby the narine tubes may be moved apart relative to one another by stretching the plastic sheath.

5. A nasal cannula as in claim 4, wherein:
the wire has a serrated outer surface for effecting a positive mechanical detent between the stretched plastic sheath and the wire.

6. A nasal cannula as in claim 2, wherein:
the wire is formed of corrosion-resistant material and has its opposite ends inserted into the opposite ends of the narine tubes.

7. A nasal cannula as in claim 1, wherein:
the bridge means comprises a saddle having a curved central portion for aiding in centering the cannula relative to the septum of the nose of the patient.

8. A nasal cannula as in claim 1, wherein:
one of the narine tubes is bent upwardly to deliver gas to the naris of a patient, and the other narine tube is bent downwardly to deliver gas to the mouth of the patient.

9. A nasal cannula as in claim 1, wherein:
both of the narine tubes are bent downwardly to deliver gas to the mouth of the patient.

* * * * *